United States Patent [19]

Williams

[11] Patent Number: Plant 6,547

[45] Date of Patent: Jan. 17, 1989

[54] MINIATURE ROSE PLANT/MINAICO

[76] Inventor: Ernest D. Williams, 1510 Lebanon Ave., Dallas, Tex. 75208

[21] Appl. No.: 43,816

[22] Filed: Apr. 29, 1987

[51] Int. Cl.[4] ..... A01H 5/00

[52] U.S. Cl. ..... Plt./10

[58] Field of Search ..... Plt./10

*Primary Examiner*—Robert E. Bagwill

[57] ABSTRACT

This invention relates to a new and distinct variety of miniature rose plant primarily identified by the unusual medium red color and the climbing habit of growth.

1 Drawing Sheet

1

The present invention relates to a new and distinct variety of hardy, dwarf, climbing type rose plant of the miniature class; the variety being primarily characterized — as to novelty — by the medium red color of the petals and the Hybrid Tea form of buds and flowers.

The variety is further characterized by:

An abundance of bloom, with flowers usually borne singly, but also several to the stem in loose clusters.

Heavy, spicy fragrance.

A plant which is vigorous, of upright climbing shape with small semi-glossy to matt foliage with pointed leaflets; the buds and flowers being similar in form and size to Golden Song (miniature — not patented).

The plant, which has a normal height of about five feet or more, can easily be maintained at lesser height by occasional trimming.

A plant which grows and blooms satisfactorily both in greenhouse and outdoors; is good for growing in pots; and provides excellent garden decoration as well as cut flowers.

The present variety of miniature rose was originated by me at Mini-Roses Nursery located at Dallas, Tex., under conditions of careful control and observation, as a cross between Golden Song (climbing miniature — not patented) as the seed parent and Magic Mist (miniature — not patented) as the pollen parent.

Subsequent to origination of the variety I successfully asexually reproduced it at Mini-Roses Nursery, located as aforesaid, by budding as well as by cuttings; the reproductions having run true in all respects.

The color photograph illustrates the variety, including the foliage, buds and flowers.

Referring now specifically to the new and distinct variety of miniature rose plant, the following is a detailed description thereof in outline; all major color plate identifications being by reference to The Royal Horticultural Society Colour Chart, except where common terms of color definition are employed.

Type: Hardy; climbing; bushy; upright; seedling; greenhouse; outdoors; cut flowers; garden decoration; potted plant.

Class: miniature. Variety identification: MINAICO (Commercial synonym: RED DELIGHT).

Flowers borne: Singly and several together (3 to 5) on sturdy stems.

Quantity of bloom: Abundant both outside and in greenhouse.

Bud:

*Peduncle.*—medium to short; slender but sturdy; erect; medium green, sometimes tinted bronze

2

(outdoors); with no prickles and few or no short haris. Before calyx breaks;

*Size.*—small. Form long; pointed with several foliaceous apendages on surface of bud; with foliaceous parts extending beyond the tip of the bud equal to one-half or less of its length.

*Color.*—medium to dark green, occasionally tinted with bronze (outdoors). As calyx breaks, color — red.

*Opening.*—opens well in all weather.

Bloom:

*Size when fully open.*—Small, averaging about 36 to 42 mm ($1\frac{1}{2}$ to $1\frac{3}{4}$").

*Petalage.*—double — averaging about 33 petals arranged regularly plus several small petaloids.

*Form.*—high centered with petals rolled loosely outward and downward. Open flowers usually show stamens.

Petals: Fairly thick; satiny on inside and on outside surface.

*Shape.*—outside petals, broad lanceolate (nearly round), sometimes with acute tip; intermediate — broad lanceolate sometimes with acute tip; inside — lanceolate sometimes with acute tip.

Color: Newly opened flower from a plant grown outside (July 1985), Dallas Tex.

*Outside petal.*—Outside surface — near Red Group 46 A blending to near Red Group 45 A to near Red Group 46 B near base of petal with a small yellow area at base. Note: Petal edges may become lighter as flower ages. Inside surface — near Red Group 46 A blending from near Red Group 46 B to near Red Group 45 B toward base, with small area of yellow at base.

*Intermediate petal.*—Outside surface similar to outside petal. Inside surface similar to outside petal.

*Inner petal.*—Outside surface — same as intermediate petal; inside surface — same as intermediate petal. General color effect; buds and newly opened flowers — deep medium red. Three days open — color deep medium red. Behavior — opens well in all weather. Old flowers tend to be less brilliant. Spent petals drop off. Flower longevity (July 1985) — plant in pot 4–6 days or longer. Cut flowers at living room temperature 4–5 days or longer.

Reproductive organs:

*Stamens.*—numerous.

*Filaments.*—average number, varying length, medium long.

*Anthers.*—numerous.

*Pollen.*—some.
*Pistils.*—average number.
*Styles.*—varying length; greenish; well formed.
*Ovaries.*—all enclosed in calyx.
*Hips.*—some.
*Sepals.*—permanent: spear shaped: recurved.
*Seed.*—few (5–8).

Foliage:

*Leaves.*—compound of five (sometimes three or seven) leaflets; medium small; leathery; semi-glossy to matt.

*Leaflets.*—shape: broad, nearly oval; apex acute; base rounded — sometimes acute. Color: medium green; new growth — normal (medium) green (sometimes tinted reddish). Rachis: medium strength; upper side may have several tiny short hairs; grooved; underside may have several thorns (1–3). Stipules: medium to short length; medium width; medium length narrow points which turn out usually at about 45 degrees or more.

Growth:

*Habit.*—climbing; bushy; upright; branched.
*Growth.*—free; vigorous; internodes short.

*Canes.*—medium; slender; sturdy.
*Main stems.*—color: medium green.
*Thorns.*—average; slender declining. Prickles — none. Hairs — none.
*Branches.*—color: medium green. Thorns: average; slender; declining. Prickles: none. Hairs — none.

The miniature rose plant and its flowers as herein described may vary in slight detail due to climatic, soil and cultural conditions under which the variety may be grown; the present description being of the variety as grown at Dallas, Tex.

The following is claimed:

1. A new and distinct variety of miniature rose plant of hardy, climbing, bushy, upright, branched habit, substantially as illustrated and described, characterized by buds and flowers of exhibition form, essentially deep medium red in color, and further characterized by a plant of compact upright shape; vigorous, with the main stems and shoots being of average thorniness, the said plant being easy to propagate from cuttings or by budding, with an abundance of small semi-glossy to mat foliage and an abundance of flowers borne singly or several to the stem in loose clusters.

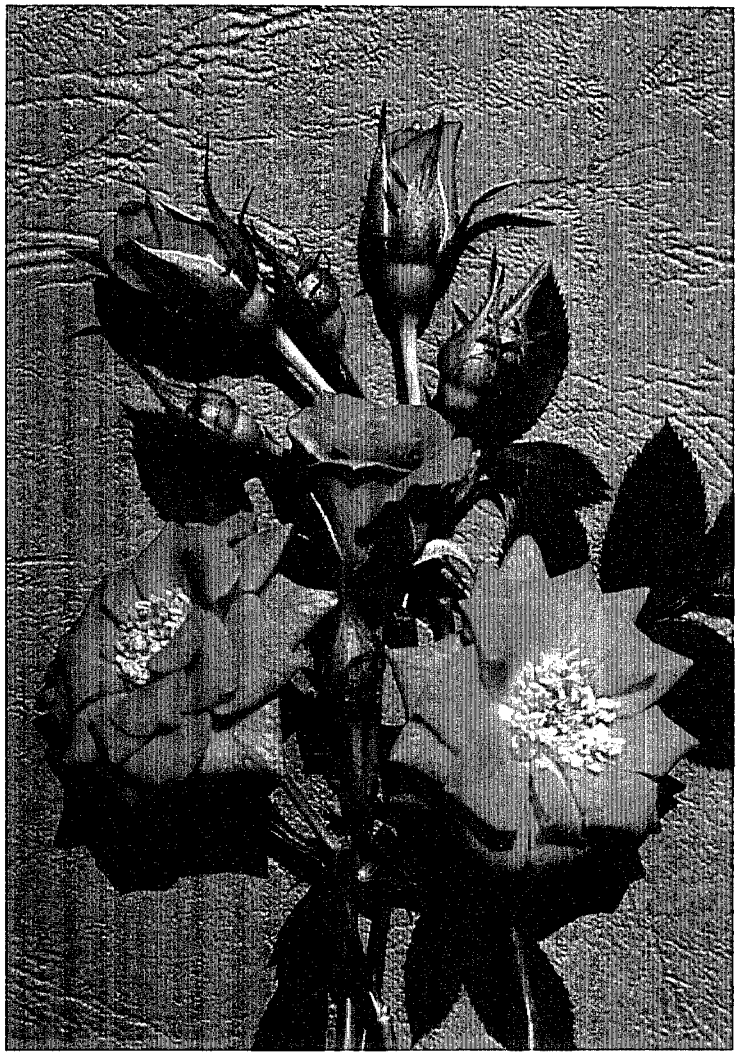

* * * * *